(12) United States Patent
Park et al.

(10) Patent No.: US 7,297,332 B2
(45) Date of Patent: Nov. 20, 2007

(54) PROTEASE, A GENE THEREFOR AND THE USE THEREOF

(75) Inventors: Ho-Yong Park, Taejon-shi (KR); Kwang-Hee Son, Taejon-shi (KR); Doo-Sang Park, Taejon-shi (KR); Sang-Woon Shin, Taejon-shi (KR); Hyun-Woo Oh, Taejon-shi (KR); Mi-Gwang Kim, Taejon-shi (KR); Dong-Ha Shin, Taejon-shi (KR)

(73) Assignee: Korean Research Institute of Bioscience and Biotechnology, Daejeon (KR)

( * ) Notice: Subject to any disclaimer, the term of this patent is extended or adjusted under 35 U.S.C. 154(b) by 399 days.

(21) Appl. No.: 09/958,321

(22) PCT Filed: Dec. 29, 2000

(86) PCT No.: PCT/IB00/02058

§ 371 (c)(1),
(2), (4) Date: Oct. 3, 2001

(87) PCT Pub. No.: WO01/57222

PCT Pub. Date: Aug. 9, 2001

(65) Prior Publication Data

US 2004/0162417 A1    Aug. 19, 2004

(30) Foreign Application Priority Data

Feb. 3, 2000  (KR) .................................. 2000-5479

(51) Int. Cl.
| | | |
|---|---|---|
| A61K 38/43 | (2006.01) | |
| C07K 1/00 | (2006.01) | |
| C12N 9/00 | (2006.01) | |
| C12N 9/52 | (2006.01) | |

(52) U.S. Cl. ..................... 424/94.1; 435/183; 435/220; 530/350

(58) Field of Classification Search ............... 424/94.1; 435/183, 220; 530/350
See application file for complete search history.

(56) References Cited

U.S. PATENT DOCUMENTS 4,931,544 A * 6/1990 Katre et al. ................. 530/351

FOREIGN PATENT DOCUMENTS

KR             220091       * 10/1999

* cited by examiner

*Primary Examiner*—Mark Navarro
(74) *Attorney, Agent, or Firm*—Sheridan Ross P.C.

(57) ABSTRACT

The present invention relates to a protease, and more specifically to a protease derived from *Aranicola proteolyticus*, a gene coding for said enzyme, a gene expression system for said protease, a process for purifying the protease, and the uses of said protease in industrial applications, such as for example, detergents, cosmetics, leather processing agents, chemicals for laboratory research, solubilizing or softening agents for food, meat modifier, feed or food additives, or oil and fat separating agents, as well as pharmaceutical compositions.

16 Claims, 4 Drawing Sheets

Fig. 4

```
   1 cgagcgcgaaagacccggaaggcacgaggtgattagtcaaaaaaagaaaatgttattcctgcgggaactaaaaagtaccggcggctaataataaagagtt
 101 attaatctataacgctttagccaaatttaacttttagccgtctaaatcccagcacgattcgcttggctctgcaggccgcattttttgttggagtttgttac
 201 caactcatggcatttaagtttcattaatattgtaaataatgcaaaaaaccagcataaatcccccttcgtaacgataataaatggctgattattttatgtgc
                                                                                                     -35
 301 agttttacaccgctgcctataattggaatcgattaccatttatggtggtaatcttatttgctgatatatatgcattaattctctctaacacactgccggt
                           -10
 401 ancggcgcataaactccttcccgtaagcgtgcggttcgttctccgtggcttcctggcaggttatgtctatctgtctgattgaaaccaatcagctaatgag
 501 tggaatcgaaccaATGCAATCTACTAAAAAGGCAATTGAAATTACTGAATCCAGCCTTGCGGCTGCGAGCTCCGCTTACAATGCAGTAGATGATTTGCTG
      -50           M  Q  S  T  K  K  A  I  E  I  T  E  S  S  L  A  A  A  S  S  A  Y  N  A  V  D  D  L  L
 601 CATTATCATGAGCGAGGCAACGGGATTCAGGTTAATGGCAAGGACTCATTTTCTACCGAACAAGCCGGGCTGTTTATTACCCGCGAGAACCAAACCTGGA
  30  H  Y  H  E  R  G  N  G  I  Q  V  N  G  K  D  S  F  S  T  E  Q  A  G  L  F  I  T  R  E  N  Q  T  W
 701 ACGGTTATAAAGTTTTTGGCCAACCGGTTAAATTAACGTTCTCTTTCCCGGATTATAAATTCTCTTCCACCAACGTCGCCGGCGATACCGGACTGAGCAA
  63  N  G  Y  K  V  F  G  Q  P  V  K  L  T  F  S  F  P  D  Y  K  F  S  S  T  N  V  A  G  D  T  G  L  S  K
 801 ATTCAGCGCGGAACAGCAGCAGCAGGCTAAGCTGTCGCTGCAGTCCTGGTCTGACGTGGCCAATATCACCTTTACGGAAGTTGGTGCCGGCCAGAAGGCC
  97  F  S  A  E  Q  Q  Q  Q  A  K  L  S  L  Q  S  W  S  D  V  A  N  I  T  F  T  E  V  G  A  G  Q  K  A
 901 AATATCACCTTCGGTAACTACAGCCAGGATCGTCCCGGCCATTATGACTACGATACCCAGGCTTACGCCTTCCTGCCGAACACCATTTATCAGGGCCAAA
 130  N  I  T  F  G  N  Y  S  Q  D  R  P  G  H  Y  D  Y  D  T  Q  A  Y  A  F  L  P  N  T  I  Y  Q  G  Q
1001 ACCTGGGCGGGCAGACTTGGTACAACGTCAACCAGTCCAACGTGAAACATCCGGCCAGCGAAGACTACGGCCGCCAGACCTTTACCCACGAGATTGGCCA
 163  N  L  G  G  Q  T  W  Y  N  V  N  Q  S  N  V  K  H  P  A  S  E  D  Y  G  R  Q  T  F  T  H  E  I  G  H
                                                                                                 *       *
1101 TGCGTTGGGCTTGAGCCATCCGGGCGATTACAACGCCGGCGAAGGCAACCCGACTTACGAGATGCCAGCTACGCCGAAGATACTCGTGAGTTCAGCCTG
 197  A  L  G  L  S  H  P  G  D  Y  N  A  G  E  G  N  P  T  Y  R  D  A  S  Y  A  E  D  T  R  E  F  S  L
1201 ATGAGTTACTGGAGCGAAACCAACACCGGTGGCGACAACGGCGGGCACTACGCTGCGGCGCCACTGCTGGATGACATTTCCGCTATTCAGCATCTGTATG
 230  M  S  Y  W  S  E  T  N  T  G  G  D  N  G  G  H  Y  A  A  A  P  L  L  D  D  I  S  A  I  Q  H  L  Y
                                           **
1301 GTGCCAACCAGACCACCCGTACCGGCGATACCGTGTATGGCTTCAACTCAAATACCGGACGTGACTTCCTCAGTACCACCAGCAATCCGCAAAAAGTGAT
 263  G  A  N  Q  T  T  R  T  G  D  T  V  Y  G  F  N  S  N  T  G  R  D  F  L  S  T  T  S  N  P  Q  K  V  I
1401 CTTTGCGGCCTGGGATGCGGGTGGTAATGACACCTTCGATTTCTCCGGTTACACCGCTAACCAGCGTATTAATCTGAACGAGAAATCTTTCTCCGACGTG
 296  F  A  A  W  D  A  G  G  N  D  T  F  D  F  S  G  Y  T  A  N  Q  R  I  N  L  N  E  K  S  F  S  D  V
                                                                                  *
1501 GGTGGGCTGAAAGGCAACGTGTCCATTGCCGCAGGTGTGACCATCGAGAACGCGATTGGCGGTTCAGGCAATGACGTGATCGTCGGCAATGCGGCCAACA
 330  G  G  L  K  G  N  V  S  I  A  A  G  V  T  I  E  N  A  I  G  G  S  G  N  D  V  I  V  G  N  A  A  N
1601 ACGTGCTGAAAGGTGGCGCGGGCAACGACGTGCTGTTCGGCGGTGGTGGGGCTGATGAGCTGTGGGGCGGTGCGGGCAAAGACACCTTTGTCTTCTCTGC
 363  N  V  L  K  G  G  A  G  N  D  V  L  F  G  G  G  G  A  D  E  L  W  G  G  A  G  K  D  T  F  V  F  S  A
1701 GGTCAGCGATTCTGCGCCGGGTGCCTCCGACTGGATCAAGGATTTCCAGAAAGGCATCGATAAAATCGACCTGTCATTCTTCAATCAGGGCGCGCAGGGT
 397  V  S  D  S  A  P  G  A  S  D  W  I  K  D  F  Q  K  G  I  D  K  I  D  L  S  F  F  N  Q  G  A  Q  G
                                                                                                    →
1801 GGCGATCAGATCCACTTCGTCGATCATTTCAGTGGCGCAGCGGGCGAAGCCTTGCTGTCTTACAATGCGTCGAATAACGTCAGCGATCTGGCCCTGAATA
 430  G  D  Q  I  H  F  V  D  H  F  S  G  A  A  G  E  A  L  L  S  Y  N  A  S  N  N  V  S  D  L  A  L  N
              ←
1901 TCGGCGGCCATCAGGCCCCGGACATCCTGGTGAAGATCGTCGGCCAGGTTGATGTCGCCACTGACTTTATCGTTTAAcagtgcaggtgctaacgcccggc
 463  I  G  G  H  Q  A  P  D  I  L  V  K  I  V  G  Q  V  D  V  A  T  D  F  I  V  ***
2001 gccggttggccgggcgttatacaggagacgatatgaagggcagcttagcgcacgccgccttagtggcaggcggcatgatggttacggggcagttatggc
2101 cagcagtttggttcttcccagcgcgcaatcattggcggggcaatggctggtcgccaatgccgaacaacaatgtcagattgagttttttggccggtgaacag
2201 agtgaaatcaacggctactcattggttgatcggcagcactgtttggaaaaggtgttaaccgccgaggtggtcggttggcgccctgcacggacggcatcg
2301 ctttgctgcgggcggatggcagtacgctggcgttcttctcgcgatggcgatatttaccgcaaccagcttggcgcggatgacggactgacgctgaaagc
2401 gctggtataacaacagcgggttcggcagtcgaacccgccctgagcagccttacagatacagcgaacgtacgatcaggaaat
```

PROTEASE, A GENE THEREFOR AND THE USE THEREOF

CROSS-REFERENCE TO RELATED APPLICATIONS

This application is a national stage application under 35 U.S.C. § 371 of PCT Application Ser. No. PCT/IB00/02058, filed Dec. 29, 2000, which claims the benefit of priority under 35 U.S.C. § 119(a) from Republic of Korea Patent Application No. 2000/000005479, filed Mar. 2, 2000.

TECHNICAL FIELD

The present invention relates to a protease, and more specifically to a protease derived from *Aranicola proteolyticus*, a gene coding for said enzyme, a gene expression system comprising said gene, a process for purifying the protease, and the use of the protease in industrial applications.

BACKGROUND ART

Protease is an enzyme which catalyzes hydrolysis of peptide bond in proteins or peptides, exists in all organisms and plays a variety of physiological roles. Most of proteases from microorganisms are secreted to the extracellular environment and their activities are inhibited or activated by carbon sources or nitrogen sources. In addition, most of microbial proteases have their origin to pathogenic microbes to animals or plants, or the proteases have a pathogenic property.

Microbial proteases are classified according to such characteristics as temperature, optimal pH, and the residues at the active site and have different industrial applications accordingly. For example, proteases are classified into thermostable, mesophilic or thermophilic based on temperature; into acidic, weak acidic, neutral or basic based on optimal pH; and into serine protease, cysteine protease, aspartate protease or metalloprotease based on the residues at the active site.

The enzymatic activity of proteases is regulated by metallic cations such as $Ca^{2+}$, $Zn^{2+}$, $Mg^{2+}$, $Mn^{2+}$ found at the active site of the enzymes. Most proteases are zinc-containing proteins in which zinc is essential for activity. The representative example for the protease is serrapeptase produced by *Serratia marcescens*(ATCC 21074) isolated from the intestine of *Bombyx mori* and this enzyme can be used as an anti-inflammatory agent because it has a fibrin degrading ability and a hydrolysis activity for bradykinin and histamine which are inflammatory peptides. Bacterial proteases which have been cloned and characterized hitherto include those derived from *Vibrio proteolyticus* (See, David, V. A., A. H. Deutch, A. Sloma, D. Pawlyk, A. Ally, and D. R. Durham. *Gene*. 112:107-112. 1992), *Erwinia chysanthemi* B374 prtA (See, Ghigo, J. M., and C. Wandersman. *MoL Gene. Genet*. 236:135-144. 1992), *Psudomonas aeruginisa* LasB (See, Doung, F., A. Lazdunsk, B. Cami, and Murgier. *Gene*. 121:47-54. 1992), *Serratia marcescens* PrtSM (See, Braunagel, S. C., and M. J. Benedik. *MoL Gen. Genet*. 222:446-451 1990), *Bacillus thuringiensis* (See, Lovgren, A., M. Zhang, A. Engstrom, G. Dalhammar, and R. Landen. *MoL Microbiol*. 4:2137-3146.1990), etc.

DISCLOSURE OF INVENTION

Hitherto, the present inventors have succeeded in isolating a novel microorganism having an ability to degrade proteins from the intestine of *Nephilia clavata* and named it as *Aranicola proteolyticus* HY-3(KCTC accession number: 0268BP). Specifically, the present inventors have isolated and identified a protease-producing strain of *Aranicola proteolyticus* from the intestine of *Nephila clavata* [Korean Patent Publication No. 10-220091 dated Jun. 18, 1999] and succeeded in purifying the protease which is stable at temperature between 20 to 40° C. and a pH range between 6 to 10 and having an apparent molecular weight of 51.5 kD. However, the publication was focused on the identification and characterization of the microbe in morphological and taxonomic aspects. The present inventors have continued the research on the microorganism and the protease, and as a result, found that the protein is inhibited by metalloprotease inhibitors, and shows a quite increased protein degrading activity either at low temperatures, a broad range of pH or under a high salt concentration, and that it can effectively be obtained by the use of a genetically modified expression system or a purification process fitted to the specific microorganism. The inventors have also found that the protease has a broad range of industrial applications, such as for example, detergents, cosmetics, leather processing agents, chemicals for laboratory research, solubilizing or softening agents for food, meat modifier, feed or food additives, or oil and fat separating agents, as well as pharmaceutical compositions which can be used as a digestive enzyme for improving alimentary diseases, digestive ailments or abnormal conditions after operation of a digestive organ, thrombolytic agents which lyse fibrin by directly acting onto thrombus and an anti-inflammatory enzyme for eliminating inflammatory materials or necrosis tissues which serves as an in vivo protective system or as an anti-inflammatory agent for alleviating edema after surgery and trauma, and completed the present invention.

Therefore, an object of the present invention is to provide a novel gene coding for the protease comprising the sequence described in SEQ ID No. 2 and a mutant or a variant thereof which can produce said protease or its functional equivalents Another object of the present invention is to provide a novel expression system which comprises the above gene, a mutant or a variant thereof which codes for the above protease or its functional equivalents, a constitutive promoter or a regulative promoter, as a selection marker a nutrient deficient gene such as URA3 (orotidine-5'-phosphate decarboxylase) or an antibiotic resistant gene such as Ap(Ampicilin) resistant gene, and a transcriptional terminator, and a microorganism harboring the expression system.

Further object of the present invention is to provide a protease having aforementioned characteristics and comprising the amino acidic sequence as set forth in SEQ ID NO. 1.

Still further aspect of the present invention is to provide a process for purifying said protease which comprises
a) cultivating Aranicola proteolyticus in a culture media;
b) filtering the culture media to give a supernatant; and
c) purifying the protease contained in the supernatant with a resin.

Still further aspect of the present invention is to provide the uses of the protease and the gene therefor in industrial applications, such as for example, detergents, cosmetics, leather processing agents, chemicals for laboratory research, solubilizing or softening agents for food, meat modifier, feed or food additives, or oil and fat separating agents.

In addition, the present invention provides pharmaceutical compositions which can be used as a digestive enzyme for improving alimentary diseases, digestive ailments or abnormal conditions after operation of a digestive organ, thromobolytic agents which lyse fibrin by directly acting onto thrombus and an anti-inflammatory enzyme for eliminating inflammatory materials or necrosis tissues which serves as an in vivo protective system or as an anti-inflammatory agent for alleviating edema after surgery and trauma, and which comprises as an active agent the protease, enzyme variant or mutant enzyme thereof and a pharmaceutically acceptable carrier.

Further objects and advantages of the invention will become apparent through reading the remainder of the specification.

BRIEF DESCRIPTION OF DRAWINGS

The present invention is further illustrated by reference to the accompanying drawings, in which;

FIG. 4 represents a DNA sequence coding for the protease of the invention and the corresponding amino acid sequence of the protein Best Mode For Carrying Out The Invention Hereinafter, the invention will be illustrated in more detail.

Figure 1:
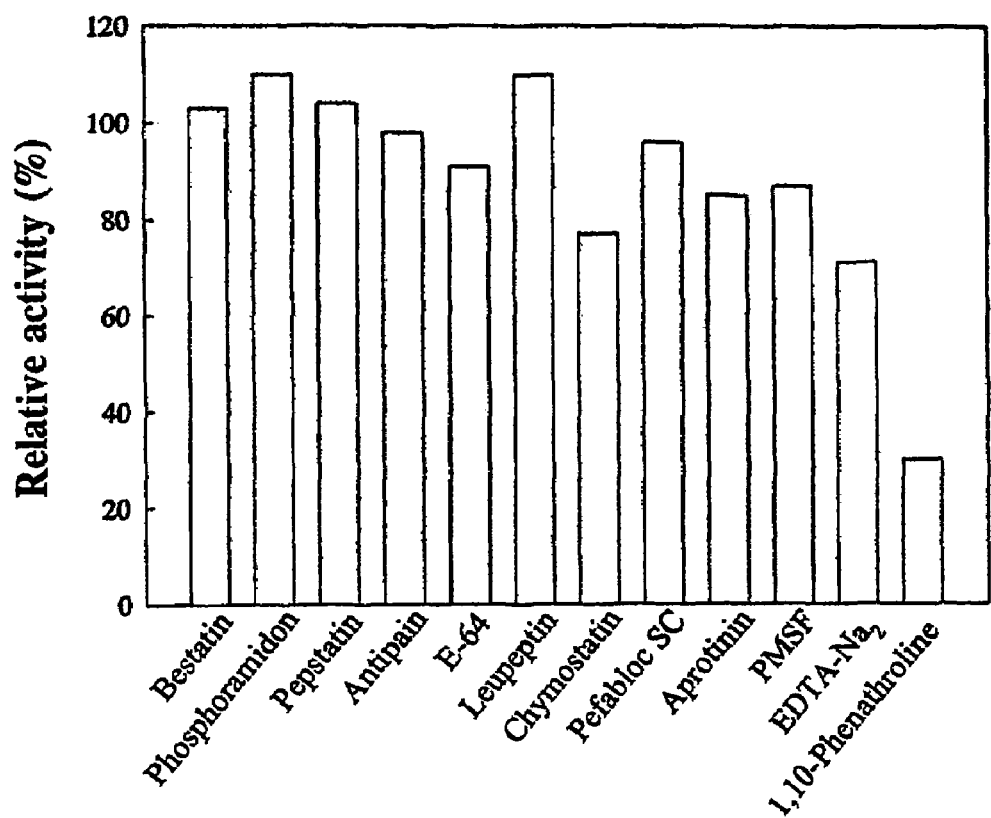
FIG. 1 represents inhibitory effects of the protease derived from *Aranicola proteolyticus* by various inhibitors. Protease was prepared according to the procedure described in Example 1, using azokazein as a substrate.

The present invention, in an aspect, provides a novel gene coding for the protease comprising the sequence described in SEQ ID NO. 2 and a mutant or a variant thereof which can produce said protease and its functional equivalents.

The gene of the invention has a nucleotide sequence as set forth in SEQ ID NO. 2 of the attached sequence listing and its size is 2.48 kb. The gene has an ORF(open reading frame) consisting of 1,461 base pairs, a −35 region (TGTGCA) and a −10 region (TATAAT) with a space of 16 base pairs in the upstream and Shine-Dalgarno (SD) sequence known as a ribosome binding site before the initiation codon. TAA is used as a stop codon and a palindromic sequence suspected as the transcription termination site appears in the downstream. This gene is isolated from *Aranicola proteolyticus* HY-3.

*Aranicola proteolyticus* HY-3 (KCTC 0268BP) was received for deposit on Jul. 29, 1996, by the Korean Collection for Type Cultures, Korea Research Institute of Bioscience & Biotechnology, Yusong, Taejon 305-333, Republic of Korea, as KCTC Deposit No. KCTC 0268BP, under the terms of the Budapest Treaty on the International Recognition of the Deposit of Microorganisms for the Purpose of Patent Procedure.

The term used herein, "a mutant or a variant thereof" is meant by a mutated gene in which a single base or two or more bases have been changed by a mutation such as, for example, substitution, deletion, addition or insertion, but still can produce the same protease or its functional equivalents. Therefore, those skilled in the art would easily appreciate that the mutant or variant can be encompassed within the scope of the present invention. Generally, a mutant or variant having about 80% or more of homology in the case of the protease and the gene of the invention, and preferably 90% or more of homology can be encompassed in the contexts of the invention, a mutant or a variant thereof.

The present invention, in an another aspect, provides a novel expression vector which comprises a gene coding for the above protease, a mutant or a variant thereof which codes for the protease or its functional equivalents, a constitutive promoter or a regulative promoter, as a selection marker, a nutrient deficient gene such as URA3 (orotidine-5'-phosphate decarboxylase) or an antibiotics resistant gene, such as Ap(Ampicilin) resistant gene, and a transcriptional terminator and a microorganism transformed with the expression vector.

The vector system containing the gene coding for the protease and the transformant can be prepared according to the conventional recombinant DNA technology known to those skilled in the art, in which, for example, a DNA fragment containing the sequence coding for the aforementioned protease is isolated from the wild type strain such as *Aranicola proteolyticus* and is cloned into a suitable regulatory elements together with a suitable expression signal, and the resulting vehicle is then introduced into an autonomously replicating plasmid or into a chromosome of bacteria.

A series of such steps constituting the conventional recombinant processes have essentially been known in the art, and for example one can easily accomplish the purpose by employing those processes taught by Maniatis et al., Molecular Cloning: A Laboratory Manual 8.11-8.13 (The 2nd ed., Cold Spring Harbor Laboratory Press (1989)].

The present invention further provides a protease having the aforementioned characteristics and comprising the amio acid sequence as set forth in SEQ ID NO. 1, or an enzyme variant or a mutant enzyme thereof.

The term used herein, "an enzyme variant or a mutant enzyme" is meant by the functionally same enzyme as the protease in which a single amino acid or a plurality of the amino acids have been modified or changed due to the changes in DNA nucleotide sequence(s) of the parental gene or the derivatives thereof. Though preferable protease according to the invention can be derived from *Aranicola proteolyticus*, for example, *Aranicola proteolyticus* HY3-1, the functionally equivalent protease can be obtained from a form of a variant or a mutant thereof using a vector system and a suitable host microorganism which may essentially not be the same organism from which the parental gene has been derived.

The present inventors isolated and purified the protease produced from *Aranicola proteolyticus*, analyzed enzymological characteristics thereof, and carried out gene cloning and sequencing therefor. As a result, the amino acid sequence of the protease as set forth in SEQ ID NO: 1 showed 92.6% similarity to the protease derived from *Serratia marcescens* SM6. In addition, amino acid sequence at the $Zn^{2+}$binding site and the active site which exist in most metalloproteases was found to be well conserved. The relative activity of the protease became lowered in the presence of equal concentrations of metalloprotease inhibitors, for example EDTA and phenanthroline (See, FIG. 1).

Figure 2:
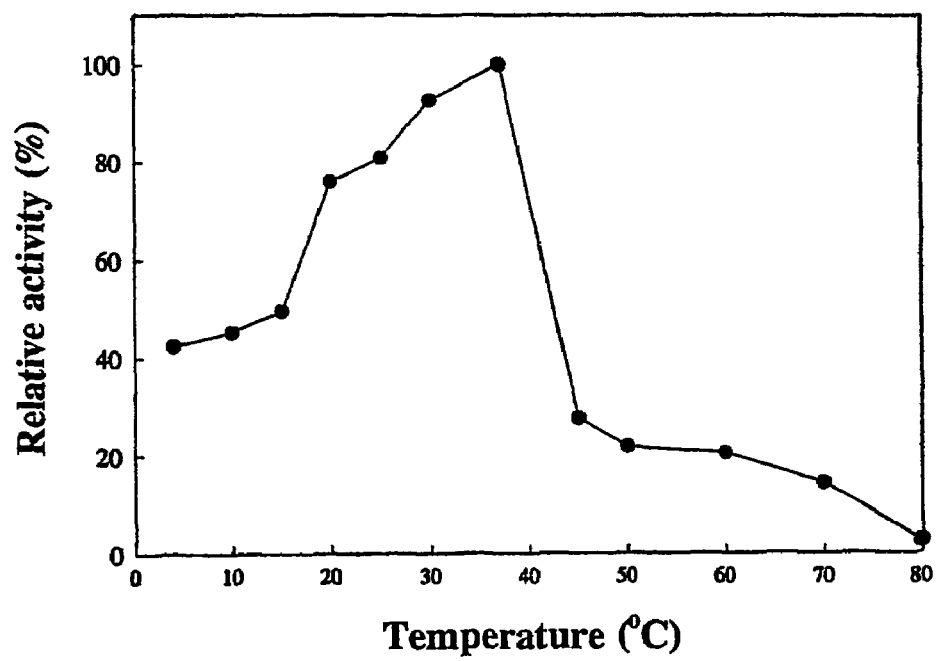
FIG. 2 represents heat stability of the protease from *Aranicola proteolyticus*. Protease was prepared according to the procedure described in Example 1, using azokazein as a substrate.
Figure 3:
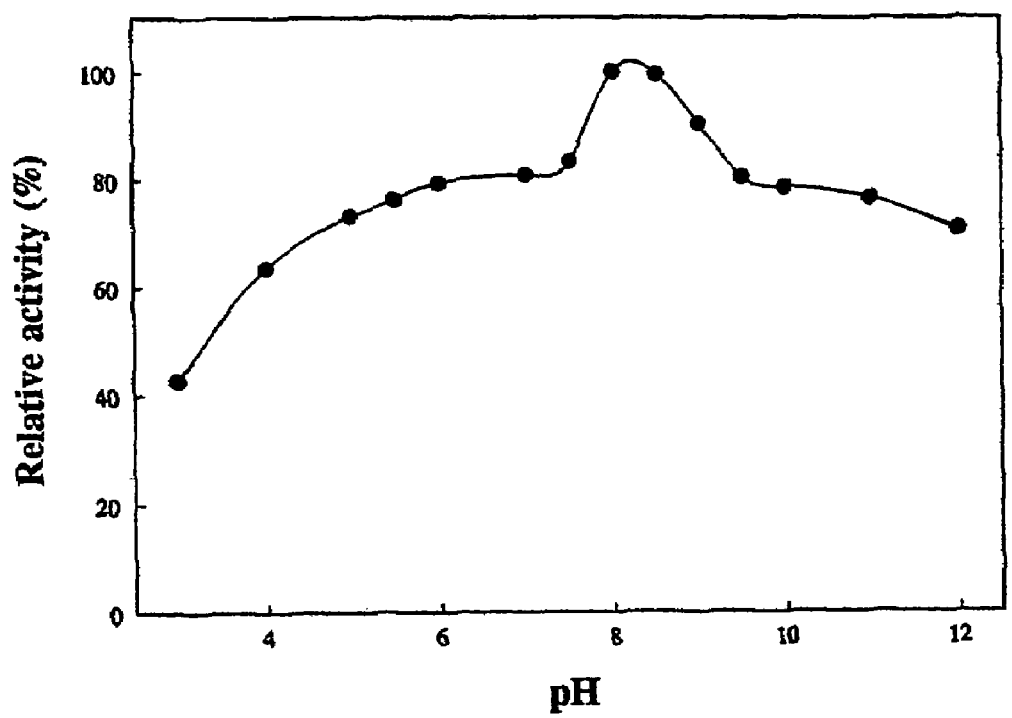
FIG. 3 represents activity and stability of the protease at different pH. Protease was prepared according to the procedure described in Example 1, using azokazein as a substrate.

These observations support that the protease is a zinc-binding metalloprotease requiring zinc ion($Zn^{2+}$) for its activity. Besides, according to the test in which its relative activity was measured at different temperatures ranging from 4° C. to 80° C., the maximum activity was observed at 37° C. and at least 75% of relative activity was observed at temperatures between 20° C. to 40° C. (See FIG. 2). Relative activity measured for a substrate, azokazein at different pH showed the maximum activity at pH 8.0; whereas at least 80% of the maximum activity at pH 7.0 to 9.5(See FIG. 3). SDS-PAGE(Sodium dodecyl sulfate-poly acrylamide gel) electrophoresis of the enzyme showed that the protease band had an apparent molecular weight of about 51.5 kDa.

Therefore, the protease according to the present invention has an apparent molecular weight of 51.5 kDa and the optimal temperature for activity at 20° C. to 37° C. (at pH 7.6) and an optimal pH at 7.0 to 9.5 (at 37° C.). The protease retains high activity under high salt concentrations and inhibited by metalloprotease inhibitors such as EDTA and phenanthroline.

The present invention further provides a process for purifying the protease which comprises
 a) cultivating *Aranicola proteolyticus* in a culture media;
 b) filtering the culture media to give a supernatant; and
 c) purifying the protease contained in the supernatant with a resin.

In one embodiment of the present invention, the protease can be produced by cultivating *Aranicola proteolyticus* in a suitable nutrient medium containing a nitrogen source and inorganic salts followed by recovering the protease, or by using the conventional recombinant DNA technologies.

*Aranicola proteolyticus* HY-3 is a mobile aerobic Gram-negative bacterium. It is globular in shape with 0.5 to 0.8 mm in diameter. Its growth response was positive in the presence of catalase and negative in the presence of oxidase.

The microorganism can be cultured in a medium containing assimilable carbon sources and nitrogen sources with other essential nutrients. The culture medium can be prepared in a conventional manner. The extracellular protease produced in the fermentation broth can be recovered and purified by the conventional method known to the art.

In order to isolate the protease of the invention, *Aranicola proteolyticus* is first cultured as aforementioned. The bacterial pellet and the supematant are separated and the supernatant is then concentrated. The concentrated solution is purified using resins. In a preferred embodiment, the purification of the concentrated solution is carried out by an ion exchange resin using DEAE-cellulose and a gel filtration exchange resin using Sephadex G-75 which is pretreated with Tris-HCl buffer. Finally, a preservative is optionally added to the purified protease.

In another embodiment of the present invention, the protease can be produced by the conventional recombinant DNA technology in which, for example, a DNA fragment containing the sequence coding for aforementioned protease is isolated from the wild type strain such as *Aranicola proteolyticus* and is cloned into a suitable regulatory elements together with a suitable expression signal, and the resulting vehicle is then introduced into an autonomously replicating plasmid or into a chromosome of bacteria. The bacteria is then cultured in a medium optimized to express the protease and the protease is recovered from the medium by aforementioned method. Preferable host organism, but not limited thereto, includes, for example, *E. coil, Bacillus, Aspergillus, Streptomyces* or *Saccharomyces*.

The present invention, in a still further aspect, provides the uses of the protease in industrial applications, such as for example, detergents, cosmetics, leather processing agents, chemicals for laboratory research, solubilizing or softening agents for food, meat modifier, feed or food additives, or oil and fat separating agents, as well as pharmaceutical compositions which can be used as a digestive enzyme for improving alimentary diseases, digestive ailments or abnormal conditions after operation of a digestive organ, thrombolytic agents which lyse fibrin by directly acting onto thrombus and an anti-inflammatory enzyme for eliminating inflammatory materials or necrosis tissues which serves as an in vivo protective system or as an anti-inflammatory agent for alleviating edema after surgery and trauma Proteolytic property of The protease of the invention can be used in detergent industry. In a preferred embodiment of the protease utility, the present invention provides a detergent composition comprising the protease according to the invention, other enzymatic ingredients and additives.

The enzymatic ingredients known to the art, but not limited thereto, include one or more other enzymes selected from the group consisting of amylases, lipases, cellulases, oxidases, peroxidases and/or the mixture thereof.

The detergent composition of the invention may comprise one or more surfactants, which may be of an anionic, non-ionic, cat-ionic, amphoteric or zwitterionic type, or a mixture of these. Typical examples of anionic surfactants include linear alkyl benzene sulfonates (LAS), alkyl sulfates (AS), alpha olefin sulfonates (AOS), alcohol ethoxy sulfates (AES) and alkali metal salts of natural fatty acids. Examples of non-ionic surfactants include alkyl polyethylene glycol ethers, nonylphenol polyethylene glycol ethers, fatty acids esters of sucrose and glucose, and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulation aids, optical brighteners, foam boosters, chelating agents, fillers, and fabric softeners.

The detergent compositions of the invention can be formulated in any convenient form, such as powders, liquids, etc.

The protease of the invention may be included in a detergent composition by adding separate additives containing the detergent protease, or by adding a combined additive comprising different detergent enzymes.

The additive of the invention can be formulated as e.g. granules, liquids, slurries, etc. Preferred detergent additive formulations are non-dusting granules, liquids, in particular stabilized liquids, slurries, or protected enzymes. Dust free granulates may be produced e.g. according to GB Patent Publication No. 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol, a sugar or sugar alcohol, lactic acid or boric acid, according to established methods. Other enzyme stabilizers are well known in the art. Protected enzymes may be prepared according to the method disclosed in EP Patent Publication No. 238,216. In one useful embodiment the protease of the invention may be incorporated in detergent formulations according to e.g. EP Patent Publication Nos. 342,177; 368,575; 378,261; and 378,262.

In another preferred embodiment, the present invention provides a pharmaceutical composition which comprises as an active agent the protease of the invention, enzyme variant or mutant enzyme thereof and a pharmaceutically acceptable carrier.

The pharmaceutical composition of the invention can be used as a digestive enzyme for improving alimentary diseases, digestive troubles, or abnormal conditions after operation of a digestive organ, thrombolytic agents which lyse fibrin by directly acting onto thrombus and an anti-inflammatory enzyme for eliminating inflammatory materials or necrosis tissues which serves as an in vivo protective system when foreign toxic agents attack, or as an anti-inflammatory agent for alleviating edema after surgery and trauma, those having ordinary skill in the art can readily identify individuals who are suspected of suffering from such diseases, conditions and disorders using standard diagnostic techniques.

Pharmaceutical compositions according to the invention comprise a pharmaceutically acceptable carrier in combination with the protease of the invention. Pharmaceutical formulations are well known and pharmaceutical compositions comprising the protease may be routinely formulated by one having ordinary skill in the art. The mode of administration of the protease may determine the sites in the organism to which the protease will be delivered. For parenteral administration, i.e., intravenous, subcutaneous, intramuscular. Intravenous administration is the preferred route. They are best used in the form of sterile aqueous solution which may contain other solutes, for example, sufficient salts, glucose or dextrose to make the solution isotonic. For oral mode of administration, the protease of the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Other suitable pharmaceutical carriers are described in Remington's Pharmaceutical Sciences, A. Osol, a standard reference text in this field, which is incorporated herein by reference.

The concentration of the active ingredient, protease is about 10□~100 □/□ body weight per day. However, those skilled in the art would appreciate that the dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. See Gennaro, Alfonso, ed., Remington's Pharmaceutical Sciences, 18th Edition, 1990, Mack Publishing Co., Easton Pa.

The present invention, in a further preferred embodiment, provides a cosmetic composition which comprises the protease of the invention and/or acid buffer, acid protease or inorganic acid together with a cosmetically acceptable carrier, vehicle or excipient.

The cosmetically acceptable carrier, vehicle or excipient component of the acidic buffer is selected from the group consisting of lotions, tinctures, creams, emulsions, gels, ointments, water, water-workable cream, polyvinyl alcohol, hydroxyethyl cellulose, cellulose, hydrophilic acrylic polymer, emollients, skin moisturizing components, enzyme stabilizers, glycerol, surfactants, preservatives, hydrophilic thickening agents used in pharmaceutical formulations and mixtures thereof. Acid protease is selected from the group consisting of fungal proteases, bacterial proteases or mammalian proteases or mixtures thereof or selected from the group consisting of pepsin, cathepsin, human urinary acid protease, rhizopuspepsin, penicillopepsin, endothiapepsin or mixtures thereof. The representative examples of the inorganic acid is selected from the group consisting of phosphoric acid, pyrophosphoric acid, triphosphoric acid, polyphosphoric acid, sodium bisulfate, potassium bisulfate or mixtures thereof.

Further, the protease of the invention, in another preferred embodiment, can be used as leather processing agents. Therefore, it is possible to provide an acqueous enzyme preparation, or a composition which is particularly suitable for the leather industry which handles anhydrous organic solutions.

The use of protease accounts for a large part of the leather manufacturing process. Hereinbleow, the use of the protease of the invention in connection with the leather processing industry will be explained in more detail.

In order to manufacture leather products, a raw material is subjected to a soaking process, a liming process, a deliming process, a bating process, a pickling process, a tanning process, a dyeing process, a drying process and a finishing process. Among these processes, protease is used in the deliming process and bating process. The deliming process and the bating process comprise steps of neutralization and acid treatment, the condition of which being adjusted so that collagen protein in the leather skin leave undestructed. In other words, directly subjecting dehaired skin to the pickling process and the tanning process, skipping the deliming process and the bating process, may cause fatal destruction or denaturation of proteins constituting the leather skin.

The deliming process removes components in the leather skin that are unnecessary for leather processing by protease digestion. The bating process provides softness and elasticity in the skin by enzyme treatment, supplementing the deliming process which is insufficient to relax fiber tissue in the leather skin. It is this deliming process that the action of protease is considered most important.

The protease digests and elutes epidermal cells, hair roots, glandulae sudoriferae, calcium soaps, emulsified fats which left in the dehaired skin after partial hysrolysis with lime pickling, and it also clears and smooths the surface of dehaired skin. In addition, it digests and elutes various unnecessary proteins and acts on elastin fiber or reticulin fiber to modify their physicochemical properties to certain extent.

The uses of protease for laboratory research can be contemplated in various embodiments depending on its specific purposes. For example, it can be used to remove unnecessary proteins in DNA isolation and purification procedures. It can also be used in research involving protein chemistry such as amino acid sequencing.

EXAMPLES

Hereinbelow, the invention will be explained in more detail by way of the following examples. However, it is apparent that the scope of the invention shall not be limited by the examples.

Example 1

Production of Protease

In order to purify the protease of the invention, *Aranicola proteolyticus* HY-3 was cultured in a culture medium (Bactotryptone 0.5%, Yeast extract 0.5%, NaCl 0.1%, KCl 0.05%, $CaCl_2$ 0.02%, $MgCl_2$ 0.02%) at 22° C. for 18 hours. A supernatant was separated from the culture broth using 2 □ membrane filter, and then concentrated using 10 kDa membrane filter. As the protease of the invention is basically an anionic protein, the protease was purified by an ion exchange resin using DEAE-cellulose pretreated with 50 mM Tris-HCl buffer (pH 7.6) and subsequently a gel filtration exchange resin using SephadexG-75 pretreated with 20 mM Tris-HCl buffer (pH 7.6). Subsequently, the thus purified enzyme solution was analyzed by 10% SDS-PAGE to identify its band pattern. As a result, it was confirmed that the protease of the invention was a monomer having an apparent molecular weight of about 51.5 kDa.

Example 2

Sequence Determination of the Gene of the Protease of the Invention

Partial amino acid sequences of the protease obtained in the Example 1 were sequenced by an amino acid sequencing analyzer (Precise Protein Sequencing System, Applied Biosystems). Based on the amino acid sequence thus obtained as described by SEQ ID NO: 3 (Ala Glu Gln Gln Gln Gln Ala) and SEQ ID NO: 4(Ile Gly His Ala Leu Gly), PCR primers as described by SEQ ID NO: 5 (forward primer: gcggaacagc agcagcaggc) and SEQ ID NO: 6(reverse primer: gcccaacgca tggccaat) were designed. Using synthetic primers, PCR was performed in the presence of genomic DNA purified from *Aranicola proteolyticus* HY-3 as a template. As a result, a DNA fragment of 2.48 kb in length was obtained and the sequence of the PCR product was then determined. On the basis of the thus determined sequence, PCR primers as described by SEQ ID NO: 7 (ataatggccg ggacgatcct ggctgtagtt ac) and SEQ ID NO: 8 (cttacgcctt cctgccgaac accatttatc ag) were designed. Using synthetic primers, reverse PCR was performed in the presence of genomic DNA purified from *Aranicola proteolyticus* HY-3 as a template.

The gene of the invention has a nucleotide sequence as set forth in SEQ ID NO. 2 of the attached sequence listing and its size is 2.48 kb. The gene has an ORF(open reading frame) consisting of 1,461 base pairs, a −35 region (TGTGCA) and a −10 region (TATAAT) with a space of 16 base pairs in the upstream, and Shine-Dalgarno (SD) sequence known as a ribosome binding site before the initiation codon. TAA is used as a stop codon and a palindromic sequence suspected as the transcription termination site appears in the downstream.

The amino acid sequence of the protease as set forth in SEQ ID NO: 1 showed 92.6% similarity to the protease derived from *Serratia marcescens* SM6. In addition, amino acid sequence at the $Zn^{2+}$ binding site and the active site which exist in most metalloproteases was found to be well conserved.

Example 3

Experiment on Enzymatic Characteristics of the Novel Protease (1) The Effect of Protease Inhibitors on the Protease Enzyme activity of the protease was measured according to the method described by Braun & Shmitz (Braun, V. & Schmitz, G., *Arch. Microbiol.* 124, 55-61, 1980). A substrate solution was prepared by dissolving 0.24 g of azocasein in 10 ml of 50 mM phosphate buffer (pH 7.5). The 300 □ of the substrate solution was mixed with 100 □ of bacterial culture solution and reacted at 37° C. for 30 minutes. Then, 300 □ of 10% trichloride acetate was added to the reaction solution and incubated at ambient temperature for 1 hour. The reaction solution was centrifuged at 7,000 rpm until pellet and supernatant was separated substantially. After adding 30 0 of 10% sodium hydroxide (NaOH) to the supernatant, the absorbance was measured at 420 nm. The enzymatic titer was defined as 1 unit by the 1.0 fold increment of absorbance value.

In order to examine the effects of protease inhibitors on the activity of the protease, the enzyme solution was added by 1 mM each of inhibitors enumerated below and incubated at 37° C. for 5 minutes before measuring relative enzyme activity. The inhibitors tested include antopain which is an aminopeptidase inhibitor, phosphoramidon which is a metalloendopeptidase inhibitor, pepstatin which is an aspartate protease inhibitor, E-64(L-trans-exoxysuccinyl leucylamido (4-fuanidino)butane) which is a cystein inhibitor, chymostatin which is a chymotrypsin inhibitor, leupeptin, petabloc SC, aprotinin, and PMSF which are serine protease inhibitors, phenanthroline and EDTA which are metalloprotease inhibitors. The result showed that EDTA inhibited the enzyme activity by about 30% and phenanthroline by about 70% (FIG. 1).

(2) The Effects of Salts on the Protease

In order to examine effects of salts on the activity of protease, the relative enzyme activity was measured at 37° C. for 4 hours in the presence of various concentrations of sodium chloride solution ranging from 0 to 1700 mM. The relative activity was measured according to the method described in Example 3(1). For comparison, the protease derived from *Serratia marcescens* SM6 was used as a control. The results are shown in Table 1 below.

TABLE 1

| Salt concentration (mM) | The relative activity of the protease (%) | The relative activity of the prior art protease (%) |
| --- | --- | --- |
| 0 | 100 | 0 |
| 170 | 134 | 140 |
| 340 | 173 | 153 |
| 510 | 200 | 157 |
| 680 | 215 | 156 |
| 1020 | 203 | 153 |
| 1360 | 196 | 143 |
| 1700 | 155 | 150 |

As shown in Table 1, the relative activity of the protease of the invention has increased by about 1.3 to 2.0 folds in proportion to the salt concentrations.

(3) The Effect of Heat on the Activity and Stability of the Protease

In order to examine the effect of heat on the activity and stability of the protease, the relative enzyme activity was measured at temperatures ranging from 4° C. to 80° C. The measurement of the activity was performed according to the method described in Example 3(1). The results are shown in Table 2.

TABLE 2

| Temperature (° C.) | Relative activity of the protease (%) | Relative activity of prior art protease (%) |
|---|---|---|
| 4 | 43 | 0 |
| 10 | 45 | 7 |
| 15 | 50 | 10 |
| 20 | 76 | 17 |
| 25 | 81 | 21 |
| 30 | 93 | 36 |
| 37 | 100 | 70 |
| 45 | 28 | 100 |
| 50 | 22 | 50 |
| 60 | 20 | 9 |
| 70 | 14 | 0 |
| 80 | 3 | 0 |

As shown in Table 2, though the maximum relative activity was obtained at 37° C., about a half of the maximum activity of the protease was maintained even as low as at 4° C. to 15° C. See, FIG. 2). Moreover, 'Ea value' (hydrolysis of azocasein) which represents a slope value indicating an activation energy in Arrenius plot to temperature exhibited 2,432 Kcal/mole at temperatures between 4° C. and 37° C. These demonstrates that the enzyme has strong activity at low temperature.

(4) The Effect of pH on the Activity and Stability of the Protease

In order to examine the pH-dependence of the protease of the invention, the inventors prepared various substrate solution with different pH. The each substrate solution was buffered with citrate-phosphate(pH 3.0 to 7.0), sodium phosphate(pH 7.0 to 9.0), Tris-HCl(pH 7.0 to 10.0), and glysine-caustic soda(pH 9.0 to 12.0), respectively. The relative protease activity was measured after mixing enzyme with each of the above substrate solution at 37° C. for 30 minutes. The measurement of the relative protease activity was followed by the method described in Example 3(1). The results are shown in Table 3.

TABLE 3

| pH | Relative activity of the protease (%) | Relative activity of prior art protease (%) |
|---|---|---|
| 3.0 | 43 | 12 |
| 4.0 | 66 | 18 |
| 5.0 | 73 | 37 |
| 5.5 | 77 | 40 |
| 6.0 | 79 | 43 |
| 7.0 | 81 | 58 |
| 7.5 | 83 | 62 |
| 8.0 | 100 | 70 |
| 8.5 | 99 | 81 |
| 9.0 | 90 | 87 |
| 9.5 | 80 | 92 |
| 10.0 | 78 | 100 |
| 11.0 | 76 | 95 |
| 12.0 | 71 | 22 |

As illustrated in Table 3, the maximum relative enzyme activity was obtained at pH 8.0. At least 80% of maximum enzyme activity was observed at pHs ranging from 7.0 to 9.5, and even at pH of 5.0 to 12.0 at least 70% of the activity was obtained (See, FIG. 3).

(5) The Activity of the Protease on Various Substrates

In order to examine the degrading ability of the enzyme against various substrates, the enzyme reactions were performed on substrates such as albumin, casein, collagen, elastin and hemoglobin. When the degrading ability of the enzyme on albumin in 24 hour reaction is defined as 100, all the other substrates except for hemoglobin showed 20~30 in 2 hour reaction. In 24 hour reaction, all the other substrates including hemoglobin achieved at least 45. These results indicates that the protease of the invention has a broad spectrum with respect to various substrates, suggesting the utility of the enzyme in industry.

Example 5

Pharmaceutical Preparations

| Form of the preparation (tablet) | |
|---|---|
| Protease | 50 mg |
| Lactose | 80 mg |
| Starch | 17 mg |
| Magnesium stearate | 3 mg |
| Crystalline Cellulose | 10 mg |

One embodiment of the invention is the use of the protease as ingredient of the Tablets whose exemplary composition is shown above. The tablets can be prepared by the conventional method. One desirable embodiment is the tablets having the conventional enteric coating (for example, hydroxypropylmethylcellulose pthalate), sugar coating or film coating.

Example 6

Application of the Protease in the Leather Industry

A 20 g of raw skin finely cut into pieces of suitable size and 14 ml of distilled water was mixed in a 50 ml test tube. Then, 0.5% sodium bisulfite and 0.5% ammonium sulfate on the basis of the weight of skin was added thereto and the mixture was incubated for 15 minutes at 26° C. Subsequently, 0.2% of detergent and 0.5% of deliming agent was added thereto and waited for 30 minutes and 1 hour, respectively, before measuring the amount of protein eluted from the skin. In the presence of the 0.5% of protease, the protein eluted amounted to 1054 mg/ml and 1062 mg/ml after 30 minutes and 60 minutes, respectively. In the absence of the protease, the protein eluted amounted to 304.5 mg/ml and 329.5 mg/ml after 30 minute and 60 minutes, respectively. These results indicate the utility of the protease in the leather processing industry.

INDUSTRIAL APPLICABILITY

The protease of the invention has a stable enzymatic activity in a broad range of pH, temperature under high salt concentration. Therefore, it has various industrial applications, such as for example, detergents, cosmetics, leather processing agents, chemicals for laboratory research, solubilizing or softening agents for food, meat modifier, feed or food additives, or oil and fat separating agents, as well as pharmaceutical compositions.

The invention claimed is:

1. An isolated or recombinant protease comprising the amino acid sequence as described in SEQ ID NO: 1 and having at least 70% of maximum enzyme activity at a pH of 5 to 12.

2. The isolated or recombinant protease according to claim 1, wherein the protease has been isolated by DEAE ion exchange chromatography and gel filtration.

3. The isolated or recombinant protease according to claim 1, wherein the protease has been isolated from *Aranicola proteolyticus*.

4. The isolated or recombinant protease according to claim 1, wherein the protease has been isolated from *Aranicola proteolyticus* HY-3 (KCTC 0268 BP).

5. The isolated or recombinant protease according to claim 1, wherein the protease is a metalloprotease having metallic cation binding sites at its active site.

6. The isolated or recombinant protease according to claim 1, which shows optimum enzymatic activity at temperature between 20 to 40 C or at pH between pH 6 to 10.

7. The isolated or recombinant protease of claim 1, which is of a purity to elute from a chromatography column and apear as a single band on an SDS-PAGE gel.

8. The isolated or recombinant protease of claim 1, which is a recombinant protease.

9. A pharmaceutical composition comprising the isolated or recombinant protease of claim 1 and a pharmaceutically acceptable carrier, wherein the pharmaceutical composition can be used as: a digestive enzyme for improving alimentary diseases, digestive ailments or abnormal conditions after operation of a digestive organ; a thromobolytic agent which lyses fibrin by directly acting on thrombus;
an anti-inflammatory enzyme for eliminating inflammatory materials or necrotic tissues which serves as an in vivo protective system; or an anti-inflammatory agent for alleviating edema after surgery and trauma.

10. The pharmaceutical composition according to claim 9, which is used for treating a digestive ailment.

11. A detergent composition comprising the isolated or recombinant protease of claim 1.

12. The detergent composition according to claim 11, further comprising one or more other enzymes selected from the group consisting of amylases, lipases, cellulases, oxidases, peroxidases and a mixture thereof.

13. The detergent composition according to claim 12, which is in the form of anion-dusting granulate, a liquid, in particular a stabilized liquid, a slurry, or a protected enzyme.

14. A cosmetic composition comprising the isolated or recombinant protease of claim 1 together with a cosmetically acceptable carrier, vehicle or excipient.

15. The cosmetic composition according to claim 14, which further comprises one or more other enzymes selected from the group consisting of amylases, lipases, cellulases, oxidases, peroxidases and a mixture thereof.

16. A purified isolated or recombinant protease comprising the amino acid sequence as described in SEQ ID NO: 1 and having at least 70% of maximum enzyme activity at a pH of 5 to 12.

* * * * *

SEQUENCE LISTING

<160> NUMBER OF SEQ ID NOS: 8

<210> SEQ ID NO 1
<211> LENGTH: 487
<212> TYPE: PRT
<213> ORGANISM: Aranicola proteolyticus
<220> FEATURE:
<221> NAME/KEY: BINDING
<222> LOCATION: (192)
<223> OTHER INFORMATION: Zn binding site
<220> FEATURE:
<221> NAME/KEY: BINDING
<222> LOCATION: (196)
<223> OTHER INFORMATION: Zn binding site
<220> FEATURE:
<221> NAME/KEY: BINDING
<222> LOCATION: (323)
<223> OTHER INFORMATION: Zn binding site

<400> SEQUENCE: 1

```
Met Gln Ser Thr Lys Lys Ala Ile Glu Ile Thr Glu Ser Ser Leu Ala
  1               5                  10                  15

Ala Ala Ser Ser Ala Tyr Asn Ala Val Asp Asp Leu Leu His Tyr His
             20                  25                  30

Glu Arg Gly Asn Gly Ile Gln Val Asn Gly Lys Asp Ser Phe Ser Thr
         35                  40                  45

Glu Gln Ala Gly Leu Phe Ile Thr Arg Glu Asn Gln Thr Trp Asn Gly
     50                  55                  60

Tyr Lys Val Phe Gly Gln Pro Val Lys Leu Thr Phe Ser Phe Pro Asp
 65                  70                  75                  80

Tyr Lys Phe Ser Ser Thr Asn Val Ala Gly Asp Thr Gly Leu Ser Lys
             85                  90                  95

Phe Ser Ala Glu Gln Gln Gln Ala Lys Leu Ser Leu Gln Ser Trp
            100                 105                 110

Ser Asp Val Ala Asn Ile Thr Phe Thr Glu Val Gly Ala Gly Gln Lys
            115                 120                 125

Ala Asn Ile Thr Phe Gly Asn Tyr Ser Gln Asp Arg Pro Gly His Tyr
        130                 135                 140

Asp Tyr Asp Thr Gln Ala Tyr Ala Phe Leu Pro Asn Thr Ile Tyr Gln
145                 150                 155                 160

Gly Gln Asn Leu Gly Gly Gln Thr Trp Tyr Asn Val Asn Gln Ser Asn
                165                 170                 175

Val Lys His Pro Ala Ser Glu Asp Tyr Gly Arg Gln Thr Phe Thr His
            180                 185                 190

Glu Ile Gly His Ala Leu Gly Leu Ser His Pro Gly Asp Tyr Asn Ala
        195                 200                 205

Gly Glu Gly Asn Pro Thr Tyr Arg Asp Ala Ser Tyr Ala Glu Asp Thr
    210                 215                 220

Arg Glu Phe Ser Leu Met Ser Tyr Trp Ser Glu Thr Asn Thr Gly Gly
225                 230                 235                 240

Asp Asn Gly Gly His Tyr Ala Ala Ala Pro Leu Leu Asp Asp Ile Ser
                245                 250                 255

Ala Ile Gln His Leu Tyr Gly Ala Asn Gln Thr Thr Arg Thr Gly Asp
            260                 265                 270

Thr Val Tyr Gly Phe Asn Ser Asn Thr Gly Arg Asp Phe Leu Ser Thr
    275                 280                 285

Thr Ser Asn Pro Gln Lys Val Ile Phe Ala Ala Trp Asp Ala Gly Gly
```

```
                290                 295                 300
Asn Asp Thr Phe Asp Phe Ser Gly Tyr Thr Ala Asn Gln Arg Ile Asn
305                 310                 315                 320

Leu Asn Glu Lys Ser Phe Ser Asp Val Gly Gly Leu Lys Gly Asn Val
                325                 330                 335

Ser Ile Ala Ala Gly Val Thr Ile Glu Asn Ala Ile Gly Gly Ser Gly
                340                 345                 350

Asn Asp Val Ile Val Gly Asn Ala Ala Asn Asn Val Leu Lys Gly Gly
                355                 360                 365

Ala Gly Asn Asp Val Leu Phe Gly Gly Gly Ala Asp Glu Leu Trp
370                 375                 380

Gly Gly Ala Gly Lys Asp Thr Phe Val Phe Ser Ala Val Ser Asp Ser
385                 390                 395                 400

Ala Pro Gly Ala Ser Asp Trp Ile Lys Asp Phe Gln Lys Gly Ile Asp
                405                 410                 415

Lys Ile Asp Leu Ser Phe Phe Asn Gln Gly Ala Gln Gly Gly Asp Gln
                420                 425                 430

Ile His Phe Val Asp His Phe Ser Gly Ala Ala Gly Glu Ala Leu Leu
                435                 440                 445

Ser Tyr Asn Ala Ser Asn Asn Val Ser Asp Leu Ala Leu Asn Ile Gly
                450                 455                 460

Gly His Gln Ala Pro Asp Ile Leu Val Lys Ile Val Gly Gln Val Asp
465                 470                 475                 480

Val Ala Thr Asp Phe Ile Val
                485

<210> SEQ ID NO 2
<211> LENGTH: 2481
<212> TYPE: DNA
<213> ORGANISM: Aranicola proteolyticus
<220> FEATURE:
<221> NAME/KEY: mat_peptide
<222> LOCATION: (514)..(1977)
<223> OTHER INFORMATION: metalloprotease
<220> FEATURE:
<221> NAME/KEY: misc_feature
<222> LOCATION: (402)
<223> OTHER INFORMATION: n = a, c, g or t

<400> SEQUENCE: 2
cgagcgcgaa agacccggaa ggcacgaggt gattagtcaa aaaaagaaaa tgttattcct      60
gcgggaacta aaaagtaccg gcggctaata ataaagagtt attaatctat aacgctttag     120
ccaaatttaa cttttagccg tctaaatccc agcacgattc gcttggctct gcaggccgca     180
tttttgttgg agtttgttac caactcatgg catttaagtt tcattaatat tgtaaataat     240
gcaaaaaacc agcataaatc cccttcgtaa cgataataaa tggctgatta ttttatgtgc     300
agttttacac cgctgcctat aattggaatc gattaccatt tatggtggta atcttatttg     360
ctgatatata tgcattaatt ctctctaaca cactgccggt ancggcgcat aaactccttc     420
ccgtaagcgt gcggttcgtt ctccgtggct tcctggcagg ttatgtctat ctgtctgatt     480
gaaaccaatc agctaatgag tggaatcgaa ccaatgcaat ctactaaaaa ggcaattgaa     540
attactgaat ccagccttgc ggctgcgagc tccgcttaca atgcagtaga tgatttgctg     600
cattatcatg agcgaggcaa cgggattcag gttaatggca aggactcatt ttctaccgaa     660
caagccgggc tgtttattac ccgcgagaac caaacctgga acggttataa agttttggc      720 caaccggtta aattaacgtt ctctttcccg gattataaat tctcttccac caacgtcgcc     780
```

-continued

```
ggcgataccg gactgagcaa attcagcgcg aacagcagc agcaggctaa gctgtcgctg      840
cagtcctggt ctgacgtggc aatatcacc tttaccgaag ttggtgccgg ccagaaggcc      900
aatatcacct tcggtaacta cagccaggat cgtcccggcc attatgacta cgatacccag     960
gcttacgcct tcctgccgaa caccatttat cagggccaaa acctgggcgg gcagacttgg    1020
tacaacgtca accagtccaa cgtgaaacat ccggccagcg aagactacgg ccgccagacc    1080
tttacccacg agattggcca tgcgttgggc ttgagccatc cgggcgatta caacgccggc    1140
gaaggcaacc cgacttacag agatgccagc tacgccgaag atactcgtga gttcagcctg    1200
atgagttact ggagcgaaac caacaccggt ggcgacaacg gcgggcacta cgctgcggcg    1260
ccactgctgg atgacatttc cgctattcag catctgtatg gtgccaacca gaccacccgt    1320
accggcgata ccgtgtatgg cttcaactca ataccggac gtgacttcct cagtaccacc    1380
agcaatccgc aaaaagtgat ctttgcggcc tgggatgcgg gtggtaatga caccttcgat    1440
ttctccggtt acaccgctaa ccagcgtatt aatctgaacg agaaatcttt ctccgacgtg    1500
ggtgggctga aggcaacgt gtccattgcc gcaggtgtga ccatcgagaa cgcgattggc    1560
ggttcaggca atgacgtgat cgtcggcaat gcggccaaca acgtgctgaa aggtggcgcg    1620
ggcaacgacg tgctgttcgg cggtggtggg gctgatgagc tgtggggcgg tgcgggcaaa    1680 gacaccttg tcttctctgc ggtcagcgat tctgcgccgg gtgcctccga ctggatcaag    1740
gatttccaga aaggcatcga taaaatcgac ctgtcattct tcaatcaggg cgcgcagggt    1800
ggcgatcaga tccacttcgt cgatcatttc agtggcgcag cgggcgaagc cttgctgtct    1860
tacaatgcgt cgaataacgt cagcgatctg gccctgaata tcggcggcca tcaggccccg    1920
gacatcctgg tgaagatcgt cggccaggtt gatgtcgcca ctgactttat cgtttaacag    1980
tgcaggtgct aacgcccggc gccggttggc cgggcgttat acaggagacg atatgaaggg    2040
cagcttagcg cacgccgcct tagtggcagg cggcatgatg gttacggggg cagttatggc    2100
cagcagtttg gttcttccca gcgcgcaatc attggcgggg caatggctgg tcgccaatgc    2160
cgaacaacaa tgtcagattg agttttggc cggtgaacag agtgaaatca acggctactc    2220
attggttgat cggcagcact gttttggaaaa ggtgttaacc gccgaggtgg tcggttggcg    2280
ccctgcaccg gacggcatcg cttgctgcg ggcggatggc agtacgctgg cgttcttctc    2340
gcgcgatggc gatatttacc gcaaccagct tggcgcggat gacggactga cgctgaaagc    2400
gctggtataa caacgcggg ttcggcagtc gaacccgccc tgagcagcct tacagataca    2460
gcgaacgtac gatcaggaaa t                                              2481
```

<210> SEQ ID NO 3
<211> LENGTH: 7
<212> TYPE: PRT
<213> ORGANISM: Aranicola proteolyticus

<400> SEQUENCE: 3

Ala Glu Gln Gln Gln Gln Ala
 1               5

<210> SEQ ID NO 4
<211> LENGTH: 6
<212> TYPE: PRT
<213> ORGANISM: Aranicola proteolyticus

<400> SEQUENCE: 4

Ile Gly His Ala Leu Gly

```
<210> SEQ ID NO 5
<211> LENGTH: 20
<212> TYPE: DNA
<213> ORGANISM: Artificial Sequence
<220> FEATURE:
<223> OTHER INFORMATION: primer-1

<400> SEQUENCE: 5
gcggaacagc agcagcaggc                                           20

<210> SEQ ID NO 6
<211> LENGTH: 18
<212> TYPE: DNA
<213> ORGANISM: Artificial Sequence
<220> FEATURE:
<223> OTHER INFORMATION: primer-2

<400> SEQUENCE: 6
gcccaacgca tggccaat                                             18

<210> SEQ ID NO 7
<211> LENGTH: 32
<212> TYPE: DNA
<213> ORGANISM: Artificial Sequence
<220> FEATURE:
<223> OTHER INFORMATION: primer-3

<400> SEQUENCE: 7
ataatggccg ggacgatcct ggctgtagtt ac                             32

<210> SEQ ID NO 8
<211> LENGTH: 32
<212> TYPE: DNA
<213> ORGANISM: Artificial Sequence
<220> FEATURE:
<223> OTHER INFORMATION: primer-4

<400> SEQUENCE: 8
cttacgcctt cctgccgaac accatttatc ag                             32
```